US008821915B2

(12) United States Patent
Cincotta

(10) Patent No.: US 8,821,915 B2
(45) Date of Patent: *Sep. 2, 2014

(54) THERAPEUTIC PROCESS FOR THE TREATMENT OF THE METABOLIC SYNDROME AND ASSOCIATED METABOLIC DISORDERS

(75) Inventor: Anthony Cincotta, Tiverton, RI (US)

(73) Assignee: VeroScience, LLC, Tiverton, RI (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/200,127

(22) Filed: Sep. 19, 2011

(65) Prior Publication Data

US 2012/0129783 A1 May 24, 2012

Related U.S. Application Data

(63) Continuation-in-part of application No. 10/944,617, filed on Sep. 17, 2004, now Pat. No. 8,021,681, which is a continuation-in-part of application No. 10/635,841, filed on Aug. 6, 2003, now abandoned.

(60) Provisional application No. 60/402,231, filed on Aug. 9, 2002.

(51) Int. Cl.
| | |
|---|---|
| *A61K 47/00* | (2006.01) |
| *A61K 31/70* | (2006.01) |
| *A61K 31/40* | (2006.01) |
| *A23L 1/29* | (2006.01) |
| *A61K 31/198* | (2006.01) |

(52) U.S. Cl.
CPC ............... *A23L 1/293* (2013.01); *A23L 1/296* (2013.01); *A61K 31/198* (2013.01)
USPC .............................. 424/439; 514/23; 514/419

(58) Field of Classification Search
USPC ...................... 424/439; 514/23, 419
See application file for complete search history.

(56) References Cited

U.S. PATENT DOCUMENTS

| | | | | |
|---|---|---|---|---|
| 4,009,265 | A * | 2/1977 | Howard | 514/4.8 |
| 4,338,304 | A | 7/1982 | Kamimae et al. | 424/669 |
| 4,446,138 | A * | 5/1984 | Pack | 514/235.2 |
| 4,659,715 | A | 4/1987 | Meier et al. | A61K 31/44 |
| 4,749,709 | A | 6/1988 | Meier et al. | A61K 31/44 |
| 4,783,369 | A | 11/1988 | Sugata et al. | |
| 4,971,969 | A | 11/1990 | Carlier et al. | A61K 31/495 |
| 5,006,526 | A | 4/1991 | Meier et al. | A61K 31/495 |
| 5,344,832 | A | 9/1994 | Cincotta et al. | A61K 31/44 |
| 5,468,755 | A | 11/1995 | Cincotta et al. | A61K 31/44 |
| 5,585,347 | A | 12/1996 | Meier et al. | A61K 38/00 |
| 5,741,503 | A | 4/1998 | Cincotta et al. | |
| 5,744,477 | A | 4/1998 | Cincotta et al. | A61K 31/44 |
| 5,760,047 | A | 6/1998 | Cincotta et al. | A61K 31/44 |
| 5,877,183 | A | 3/1999 | Cincotta | A61K 31/44 |
| 6,004,972 | A | 12/1999 | Cincotta et al. | A61K 31/44 |
| 6,011,049 | A * | 1/2000 | Whitcomb | 514/369 |
| 6,040,292 | A | 3/2000 | Sommer | A61K 38/00 |
| 6,166,017 | A | 12/2000 | Marin | A61K 31/50 |
| 6,197,765 | B1 | 3/2001 | Vardi et al. | A61K 31/5415 |
| 6,248,375 | B1 * | 6/2001 | Gilles et al. | 426/72 |
| 6,365,176 | B1 * | 4/2002 | Bell et al. | 424/439 |
| 6,376,464 | B1 | 4/2002 | Dasseux et al. | A61K 38/00 |
| 6,410,339 | B1 | 6/2002 | Marin | G01N 33/53 |
| 6,441,036 | B1 | 8/2002 | Berge | A01N 37/02 |
| 6,506,799 | B1 | 1/2003 | Dasseux | A61K 31/075 |
| 2001/0002269 | A1 * | 5/2001 | Zhao | 426/112 |

FOREIGN PATENT DOCUMENTS

| | | | | |
|---|---|---|---|---|
| EP | 1 004 594 A1 | 5/2000 | | |
| WO | WO 96/39050 | 12/1996 | | A23L 1/29 |
| WO | WO 96/39052 | 12/1996 | | A23L 1/30 |
| WO | WO 96/39868 | 12/1996 | | A23L 1/29 |

OTHER PUBLICATIONS

Nielsen et al (Naunyn-Schmiedeberg's Archives of Pharmacology, vol. 300, Summary; 1977).
NIH Publication No. 5-4642 [online], www.diabetes.niddk.nih.gov, Jan. 2005 [retrieved on Jun. 11, 2008]. Internet: <URL: http://diabetes.niddk.nih.gov/dm/pubs/diagnos is/.
Freedman, Marjorie R., King, Janet, and Kennedy, Eileen, "Popular Diets: A Scientific Review", Obesity Research, vol. 9, Supp. 1, pp. 1S-40S (Mar. 2001).
Baba, N. Hwalla, et al., "High protein vs high carbohydrate hypoenergetic diet for the treatment of obese hyperinsulinemic subjects", International Journal of Obesity, vol. 23, pp. 1202-1206 (Nov. 1999).
Alford, B. B., et al., "The effects of variations in carbohydrate, protein, and fat content of the diet upon weight loss, blood values, and nutrient intake of adult obese women", Journal of the American Dietetic Association, vol. 90, No. 4, pp. 435-540 (Apr. 1990).

\* cited by examiner

*Primary Examiner* — Kevin E Weddington

(74) *Attorney, Agent, or Firm* — Fish & Richardson P.C.

(57) ABSTRACT

The present invention is directed to a method of treating a patient suffering from the metabolic syndrome and/or related disorders including obesity, Type 2 diabetes, pre-diabetes, hypertension, dyslipidemia, insulin resistance, endothelial dysfunction, pro-inflammatory state, and pro-coagulative state, and comprising the steps of (a) providing to the patient a dietary regimen that decreases overactive CNS noradrenergic tone; followed by (b) providing to the patient a dietary regimen that increases dopaminergic tone while maintaining the above decreased overactive CNS noradrenergic tone. The present invention is also directed to food products useful in implementing the dietary regimens.

11 Claims, No Drawings

THERAPEUTIC PROCESS FOR THE TREATMENT OF THE METABOLIC SYNDROME AND ASSOCIATED METABOLIC DISORDERS

CROSS-REFERENCE TO RELATED APPLICATIONS

This application is a Continuation-in-Part of U.S. patent Ser. No. 10/944,617 filed Sep. 17, 2004, now U.S. Pat. No. 8,021,681 which is a Continuation-in-Part of U.S. patent application Ser. No. 10/635,841 filed Aug. 6, 2003, now abandoned which claims the benefit of U.S. Provisional Application No. 60/402,231 filed Aug. 9, 2002.

BACKGROUND OF THE INVENTION

1. Field of the Invention

The present invention is directed to therapeutic processes for the treatment of obesity and associated metabolic disorders such as the metabolic syndrome, and more particularly to a planned dietary regimen that can treat obesity, metabolic syndrome, prediabetes, and Type 2 diabetes.

2. Brief Description of the Art

The incidence of overweight and obese occurrences in the U.S. and worldwide human population is reaching epidemic proportions. Obesity (commonly defined as a Body Mass Index of >30 kg/m$^2$) is often associated with a variety of pathologic conditions such as hyperinsulinemia, insulin resistance, diabetes, hypertension, and dyslipidemia, and each of these conditions contributes to the risk of cardiovascular disease. Collectively, these pathologies that tend to associate (obesity, insulin resistance, dyslipidemia, and hypertension) have been termed "the metabolic syndrome" and are a major risk factor for cardiovascular disease. More recently, the U.S. National Cholesterol Education Program has classified Metabolic Syndrome as meeting three out of the following five criteria: fasting glucose level of at least 110 mg/dl, plasma triglyceride level of at least 150 mg/dl (hypertriglycerdemia), HDL cholesterol below 40 mg/dl in men or below 50 mg/dl in women, blood pressure at least 130/85 mm Hg (hypertension), and central obesity, with central obesity being defined as abdominal waist circumference greater than 40 inches for men and greater than 35 inches for women. The American Diabetes Association estimates that 1 in every 5 overweight people suffer from Metabolic Syndrome.

According to the guidelines of the American Diabetes Association, to be diagnosed with Type 2 diabetes, an individual must have a fasting plasma glucose level greater than or equal to 126 mg/dl or a 2-hour oral glucose tolerance test (OGTT) plasma glucose value of greater than or equal to 200 mg/dl (Diabetes Care, 26: S5-S20, 2003). A related condition called pre-diabetes is defined as having a fasting glucose level of greater than 100 mg/dl but less than 126 mg/dl or a 2-hour OGTT plasma glucose level of greater than 140 mg/dl but less than 200 mg/dl. Mounting evidence suggests that the pre-diabetes condition may be a risk factor for developing cardiovascular disease (Diabetes Care 26: 2910-2914, 2003). Pre-diabetes, also referred to as impaired glucose tolerance or impaired fasting glucose is a major risk factor for the development of type 2 diabetes mellitus, cardiovascular disease and mortality. Much focus has been given to developing therapeutic interventions that prevent the development of type 2 diabetes by effectively treating prediabetes (Pharmacotherapy, 24: 362-71, 2004).

Although pharmaceutical medications exist for the treatment of diabetes, dyslipidemia, obesity, and hypertension, the combined use of such medications for the treatment of the metabolic syndrome suffer many disadvantages. Frequently, a regimen of medications to treat these pathologies is impractical, unsafe, and only modestly effective in the long term. No singular long-term effective pharmaceutical treatment for the metabolic syndrome currently exists.

A second approach to the treatment of this disorder is nutritional intervention leading to the reduction of excess adiposity (adipose tissue) via a calorie restricting diet. Inasmuch as a reduction of obesity has consistently been demonstrated to improve various pathologies of the metabolic syndrome, prodigious efforts have been made to formulate a nutritional plan that may be effective in the long-term treatment of the syndrome in the general population. The development of an optimal dietary plan to treat the metabolic syndrome has proven an elusive task. There are several reasons for this shortcoming. First, the metabolic rate of calorie-restricted obese individuals quickly decreases to match the reduced energy intake and equilibrium is reached before a reduced ideal body weight is attained. Upon an increase in food consumption following this occurrence, body fat stores cycle often back above pretreatment levels. Secondly, the source of energy in many diets is high carbohydrate/low fat in content, that can exacerbate specific aspects of the syndrome. Thirdly, empirical evidence indicates that calorie restricting dietary plans are difficult to adhere to long-term and most individuals regain weight lost on such diets within 5 years. Most importantly, an enormous body of scientific evidence indicates that the control of metabolism including the development and the reversal of the metabolic syndrome resides within the central nervous system, and is largely independent of the caloric content of the diet.

Studies of vertebrate species in the wild that undergo annual cycles of metabolism oscillating between the metabolic syndrome and normal metabolism indicate that adjustable alterations of neuroendocrine activities regulated by the hypothalamus play major roles in the regulation of metabolism. For example, many vertebrate species will undergo annual cycles of body fat store level without any change in food consumption whatsoever during the year. Moreover, many species are fattest during seasons of greatest energy expenditure, such as during the migratory periods of the year. Therefore, it is not possible to ascribe increased body fat store level in these animals strictly to increased energy input or decreased energy expenditure levels. The change in body composition appears to be a function of changes in metabolic biochemical pathways operative at different seasons. Animals increase or decrease their fat to lean mass ratio by fractionally increasing lipid synthesis or protein turnover, respectively, without necessarily having to alter energy balance.

During the fattening periods of the year, it has been observed that many species develop symptoms of the metabolic syndrome (i.e., hyperinsulinemia, insulin resistance, hyperlipidemia, and glucose intolerance) analogous to the human situation. Research in this area has identified key components of this endogenous mechanism for the regulation of metabolism (Luo, S. et al., NeuroReport vol. 8: 3495-3499, 1997; Luo, S. et al., Neuroendocrinology vol. 68: 1-10, 1998; Luo, S. et al, NeuroReport vol. 10, 2073-2077, 1999; Cincotta, A. H. et al., Am. J. Physiol. vol. 278: R435-R444, 2000; Boundy, V. A. et al., Am. J. Physiol. 279: R505-R514, 2000; Luo, S. et al., Neuroendocrinology vol 69: 160-166, 1999; Bina, K. G. et al., Neuroendocrinology vol. 71: 68-78, 2000; Kraszewski, K. Z. et al., Int. J. Molecular Med. vol: 5: 349-355, 2000). These include interactions within specific nuclei of the hypothalamus that orchestrate autonomic-neuroendocrine events that in turn interact variably to produce different organismal level physiologies (i.e., normal metabolism or the metabolic syndrome) as a function of their interaction.

By identifying differences in these neural circuits between seasonal obese, insulin resistant animals and lean, insulin sensitive animals, one may be able to identify etiologic factors in the natural development of the syndrome. Collectively, such studies may suggest that decreases in the dopamine to norepinephrine activity ratio in the hypothalamus, and especially increased noradrenergic activity within the ventromedial hypothalamus, are key neuronal components driving the induction of the metabolic syndrome irrespective of energy intake in study animals. Additional components in the syndrome include increases in the activity of corticotropin releasing hormone to stimulate the pituitary-adrenal axis and the sympathetic nervous system via the dorsomedial hypothalamus, and hypothalamic increases in neuropeptide Y activity. Such neuronal alterations concurrently stimulate increases in parasympathetic and sympathetic neuronal activities leading to increased insulin hyper-secretion, hepatic glucose production, lipid synthesis, and lipolysis (Bina, K. G. et al., Neuroendocrinology vol. 71: 68-78, 2000). As a result, the organism fattens, and becomes insulin resistant, hyperlipidemic, and hypertensive (i.e., develops the metabolic syndrome).

Although pharmacologic agents acting as neuromodulators may be applied locally to appropriate neurons in the brain to induce or reverse the metabolic syndrome by mimicking the natural neuronal activities driving each condition, it is not a practical approach to the treatment of the disorder.

U.S. Pat. No. 6,004,972 to Cincotta et al., discloses a process for the long term modification and regulation of lipid and carbohydrate metabolism—generally to reduce obesity, insulin resistance, and hyperinsulinemia or hyperglycemia, or both, by administration of a dopamine agonist, such as bromocriptine.

U.S. Pat. No. 5,877,183 to Cincotta discloses methods for the regulation and modification of lipid and glucose metabolism by administering a dopamine D1 agonist, optionally in combination with a dopamine D2 agonist, an alpha-1 adrenergic antagonist, an alpha-2 adrenergic agonist, or a serotonergic inhibitor, or optionally in combination with a dopamine D2 agonist coadministered with at least one of alpha-1 adrenergic antagonist, an alpha-2 adrenergic agonist, or a serotonergic inhibitor, and further administering a serotonin $5HT_{1b}$ agonist.

U.S. Pat. Nos. 5,744,477 and 5,760,047 both issued to Cincotta et al. disclose an improvement in a method of weight and/or body-fat reduction comprising a preferably moderate reduction in the caloric intake of a subject in need of such treatment in combination with administration of a prolactin inhibitor. Additionally, this patent discloses a method for altering and/or resetting prolactin profiles and thereby controlling one or more metabolic disorders such as obesity, excessive body fat, hyperlipidemia, hyperlipoproteinemia, hyperglycemia, hypercholesterolemia, hyperinsulinemia, insulin resistance, glucose intolerance, and Type II diabetes.

U.S. Pat. No. 5,585,347 issued to Cincotta et al. discloses methods for detecting abnormalities in prolactin daily rhythms. The disclosed methods involve comparing a prolactin profile of a vertebrate (including a human) subject being tested that has been compiled over a predetermined period to a predetermined standard prolactin profile for healthy subjects U.S. Pat. No. 5,344,832 issued to Cincotta et al. discloses a process for the long term modification and regulation of lipid and glucose metabolism to reduce obesity, insulin resistance, and hyperinsulinemia or hyperglycemia, or both, by administration of a dopamine agonist and a prolactin stimulator. The dopamine agonist and prolactin stimulator are administered in daily dosages, respectively, at a time of day dependent on the normal circadian rhythm of fat and lean members of a similar species.

What is needed in the art is an effective dietary method of treating obesity, the metabolic syndrome, and its associated disorders, including Type 2 diabetes, that is simple to implement and takes into account the neuronal effects that can influence regulatory centers for metabolism. The present invention is believed to be an answer to that need.

SUMMARY OF THE INVENTION

In one aspect, the present invention is directed a method of treating a patient suffering from the metabolic syndrome, obesity, Type 2 diabetes, pre-diabetes, hypertension, dyslipidemia, insulin resistance, endothelial dysfunction, pro-inflammatory state, pro-coagulative state, or any combination thereof, comprising the steps of: (a) providing to the patient suffering from metabolic syndrome, obesity, Type 2 diabetes, pre-diabetes, hypertension, dyslipidemia, insulin resistance, endothelial dysfunction, pro-inflammatory state, and pro-coagulative state a dietary regimen that decreases overactive CNS noradrenergic tone; followed by (b) providing to the patient a dietary regimen that increases dopaminergic tone while maintaining the decreased overactive CNS noradrenergic tone.

In another aspect, the present invention is directed to an article of manufacture comprising packaging material and one or more food products contained within the packaging material, wherein the one or more food products are effective for decreasing overactive CNS noradrenergic tone and wherein the packaging material comprises a label which indicates that the one or more food products can be used for treating metabolic syndrome, obesity, Type 2 diabetes, pre-diabetes, hypertension, dyslipidemia, insulin resistance, endothelial dysfunction, pro-inflammatory state, pro-coagulative state, or a combination thereof, in a patient, and wherein the one or more food products are selected from the group consisting of:

1) protein of about 25%±5% of total daily caloric intake of the patient;

2) monounsaturated fat of about 25%±5% of total daily caloric intake of the patient;

3) saturated fat of about 5%±5% of total daily caloric intake of the patient;

4) polyunsaturated fat of about 3%±5% of total daily caloric intake of the patient; and 5) complex carbohydrate of about 42%±7% of total daily caloric intake of the patient;

and combinations thereof.

In another aspect, the present invention is directed to an article of manufacture comprising packaging material and one or more food products contained within the packaging material, wherein the one or more food products are effective for increasing dopaminergic tone while maintaining decreased overactive CNS noradrenergic tone, and wherein the packaging material comprises a label which indicates that the one or more food products can be used for treating metabolic syndrome, obesity, Type 2 diabetes, pre-diabetes, hypertension, dyslipidemia, insulin resistance, endothelial dysfunction, pro-inflammatory state, pro-coagulative state, or a combination thereof, in a patient, and wherein the one or more food products are selected from the group consisting of:

1) protein of about 24%±5% of total daily caloric intake of the patient;

2) monounsaturated fat of about 23%±5% of total daily caloric intake of the patient;

3) saturated fat of about 5%±5% of total daily caloric intake of the patient;

4) polyunsaturated fat of about 3%±5% of total daily caloric intake of the patient;

5) complex carbohydrate of about 45%±5% of total daily caloric intake of the patient;

6) L-DOPA-containing food in an amount sufficient to ingest about 25-400 mg. of L-DOPA per day;

and combinations thereof.

In another aspect, the present invention is directed to a method of treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state, comprising the steps of: (a) providing to the patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state a food product that decreases overactive CNS noradrenergic tone; wherein the food product that decreases overactive CNS noradrenergic tone comprises:

1) protein intake of about 25%±5% of total daily caloric intake;

2) monounsaturated fat intake of about 25%±5% of total daily caloric intake;

3) saturated fat intake of about 5%±5% of total daily caloric intake;

4) polyunsaturated fat intake of about 3%±5% of total daily caloric intake;

5) complex carbohydrate intake of about 42%±7% of total daily caloric intake; and 6) total caloric intake set at 15-25% less than the patient's daily energy expenditure; followed by (b) providing to the patient a food product that increases dopaminergic tone while maintaining the decreased overactive CNS noradrenergic tone; wherein the food product that increases dopaminergic tone while maintaining the decreased overactive CNS noradrenergic tone comprises:

1) protein intake of about 24%±5% of total daily caloric intake;

2) monounsaturated fat intake of about 23%±5% of total daily caloric intake;

3) saturated fat intake of about 5%±5% of total daily caloric intake;

4) polyunsaturated fat intake of about 3%±5% of total daily caloric intake;

5) complex carbohydrate intake of about 45%±7% of total daily caloric intake;

6) total caloric intake set at 0-25% less than the patient's daily energy expenditure; and 7) L-DOPA-containing foods in an amount sufficient to ingest about 20-400 mg of L-DOPA per day; and wherein the polyunsaturated fat intake in each of steps (a) and (b) individually comprise a ratio of omega-3 to omega-6 polyunsaturated fatty acids from between about 0.25:1 to about 2:1; and wherein the providing step (a) continues for approximately 4 to 12 weeks; and wherein the providing step (b) continues for approximately 4 to 6 months.

In another aspect, the present invention is directed to a food product effective for treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state, the food product comprising: (a) nutrients that decreases overactive CNS noradrenergic tone; and (b) nutrients that increases dopaminergic tone while maintaining the decreased overactive CNS noradrenergic tone.

These and other aspect will be described in more detail in the following detailed description of the invention.

DETAILED DESCRIPTION OF THE INVENTION

It has been unexpectedly discovered by the present inventor that macro- and micro-nutrients may act as neuronal modulators and influence regulatory centers for metabolism. In other words, the foods consumed on a daily basis may influence metabolism not as a function of their caloric content but rather indirectly through modulating the control centers for metabolism in the brain. It is believed that adherence to the dietary plan will improve neuroendocrine regulation of metabolism and lead to a reduction of symptoms of the metabolic syndrome as well as related disorders such as obesity, Type 2 diabetes, pre-diabetes, hypertension, dyslipidemia, insulin resistance, endothelial dysfunction, pro-inflammatory state, and pro-coagulative state.

In seasonal animals (e.g., those animals whose physiology changes predictably and in an ordered fashion as a function of the time of the year; see Meier, A. H. and Cincotta, A. H., Diabetes Reviews, Vol. 4: 464-487, 1996 for a review), the quality of foods available for consumption changes seasonally. Even though the annual cycle of physiology is endogenous, it can be potentiated by seasonal changes in food quality. The present inventor has unexpectedly discovered that macronutrient and micronutrient influences on central control centers for metabolism are characteristic of many vertebrate species including animals such as humans. Therefore, it is believed that it is possible to influence the primary regulator of metabolism (the brain) via appropriate alterations in food quality intake and thereby influence overall metabolism. Such alterations in metabolism can be effective in treating obesity, and associated diseases such as hyperinsulinemia, cardiovascular disease, insulin resistance, diabetes, hypertension, dyslipidemia, and the like.

The hypothalamic activities described above that potentiate the metabolic syndrome induce the following neuroendocrine changes in the periphery relative to normal individuals: (1) increases in sympathetic tone, e.g., increased plasma norepinephrine to dopamine neurotransmitter or neurotransmitter metabolite ratio; (2) decreased morning urinary melatonin metabolite levels; (3) increases in plasma insulin and glucagon levels before and insulin levels during a glucose tolerance test; (4) increases in plasma norepinephrine and norepinephrine metabolite levels during the glucose tolerance test; (5) increases in plasma cortisol levels; and (6) increases in the plasma or urinary norepinephrine basal level and/or in response to corticotrophin releasing factor. A daily nutritional dietary intake regimen in accordance with the present invention is believed to be effective in reducing these hypothalamic activities and thereby treating obesity, diabetes, the metabolic syndrome, and it's associated diseases. As defined herein, the term "dietary regimen" refers broadly to packaged or unpackaged food product provided to a patient for consumption in accordance with the method of the present invention, or information in any form communicated to a patient that instructs the patient about packaged or unpackaged foods that should be consumed (e.g., dietary counseling). The term "metabolite" refers to a cellular breakdown product of a selected compound, such as a neurotransmitter. The term "regular food" and "ordinary food", used herein interchangeably, refers to food that is not part of the packaged food items of the invention. Furthermore, in the method of the present invention, the phrase "overactive CNS noradrenergic tone" refers to overactive central nervous system noradrenergic tone, and is exemplified in part by overactive sympathetic tone.

As indicated above, the present invention is directed to methods of treating a patient suffering from obesity, metabolic syndrome and/or related disorders, including Type 2 diabetes, comprising a dietary regimen that decreases overactive CNS noradrenergic tone; followed by a dietary regimen that increases dopaminergic tone while maintaining the decreased overactive CNS noradrenergic tone. Each of these dietary regimens and their associated effects are discussed in more detail below.

Since each patient's individual condition and metabolic characteristics are unique, it is desirable, although not always necessary, to first evaluate the patient's central neuronal activities so that a baseline of the patient's metabolism can be established. This evaluation is done by several means, including, but not limited to, obtaining a medical history of the patient, conducting a physical examination of the patient, calculating the patient's daily energy expenditure (e.g. Harris-Benedict equation and/or indirect calorimetry), and determining the patient's ideal body weight (e.g., insurance table of ideal body weight based on height and weight measurements and percent body fat composition, age, and sex). In addition, it is desirable to conduct a blood test to evaluate the patient's perhipheral neuroendocrine factors. Such a blood test would preferably include an analysis (e.g., a determination of the amounts) of (a) plasma norepinephrine and norepinephrine metabolite, insulin, dopamine and dopamine metabolite levels before and/or during a glucose tolerance test (GTT), (b) plasma cortisol levels, (c) morning urinary melatonin metabolite, norepinephrine or norepinephrine metabolite levels, and/or (d) plasma norepinephrine or norepinephrine metabolite levels, generally in response to corticotropin releasing factor. Another marker that may be of potential value in evaluating neuronal activities is plasma serotonin or plasma serotonin metabolite levels (e.g, 5-HIAA, 5-hydroxyindole acetic acid). Comparing the amounts of these surrogate markers between normal and metabolic syndrome subjects will delineate the neuroendocrine "blueprint" to be reestablished by dietary intervention in metabolic syndrome subjects. In addition, periodic inspections of these markers during the course of dietary intervention will allow for re-adjustment of the dietary plan to achieve optimal success in improving metabolism.

In one embodiment, the dietary regimen that decreases overactive CNS noradrenergic tone (hereinafter referred to as Stage 1) preferably includes:
1) protein intake of about 25%±5% of total daily caloric intake;
2) monounsaturated fat intake of about 25%±5% of total daily caloric intake;
3) saturated fat intake of about 5%±5% of total daily caloric intake;
4) polyunsaturated fat intake of about 3%±5% of total daily caloric intake;
5) complex carbohydrate intake of about 42%±7% of total daily caloric intake; and
6) total caloric intake set at 15-25% less than the patient's daily energy expenditure.

More preferably, the dietary regimen that decreases overactive CNS noradrenergic tone includes:
1) protein intake of about 25%±3% of total daily caloric intake;
2) monounsaturated fat intake of about 25%±3% of total daily caloric intake;
3) saturated fat intake of about 5%±3% of total daily caloric intake;
4) polyunsaturated fat intake of about 3%±3% of total daily caloric intake;
5) complex carbohydrate intake of about 42%±5% of total daily caloric intake; and
6) total caloric intake set at 15-20% less than the patient's daily energy expenditure.

Nutrients that decreases overactive CNS noradrenergic tone include pantethine, neuronal noradrenaline synthesis inhibitors, neuronal postsynaptic noradrenergic receptor blockers, neuronal presynaptic noradrenaline reuptake enhancers, neuronal presynaptic noradrenaline receptor stimulators, neuronal presynaptic noradrenaline release inhibitors, noradrenaline degradation enzyme stimulators, neuronal postsynaptic noradrenaline signal transduction inhibitors, and combinations thereof.

The length of time spent in Stage 1 is determined from the blood test results established prior to beginning the dietary regimen. In general, when either (a) the plasma norepinephrine, norepinephrine metabolite, and/or insulin levels, (b) morning urinary norepinephrine metabolite levels, (c) glucose tolerance norepinephrine levels, or (d) plasma norepinephrine to dopamine neurotransmitter or neurotransmitter metabolite ratio are reduced at least 20% of initial values, the individual is ready to begin Stage 2 of the program. This process generally takes approximately 4 to 12 weeks depending on the individual.

At the end of Stage 1, sympathetic nervous system activities overactive in the metabolic syndrome will become reduced towards normal levels, thus improving metabolism. This can be evidenced in part via measures of plasma norepinephrine metabolite and norepinephrine levels before and during a glucose tolerance test as mentioned above. At this time, the dietary regimen that increases dopaminergic tone while maintaining decreased overactive CNS noradrenergic tone (hereinafter referred to as Stage 2) commences, and preferably includes one or more of the following:
1) protein intake of about 24%±5% of total daily caloric intake;
2) monounsaturated fat intake of about 23%±5% of total daily caloric intake;
3) saturated fat intake of about 5%±5% of total daily caloric intake;
4) polyunsaturated fat intake of about 3%±5% of total daily caloric intake;
5) complex carbohydrate intake of about 45%±7% of total daily caloric intake;
6) total caloric intake set at 15-25% less than the patient's daily energy expenditure; and
7) L-DOPA-containing foods (such as Broad beans) in an amount sufficient to ingest about 20-400 mg of L-DOPA per day.

More preferably, the Stage 2 dietary regimen includes one or more of the following:
1) protein intake of about 24%±3% of total daily caloric intake;
2) monounsaturated fat intake of about 23%±3% of total daily caloric intake;
3) saturated fat intake of about 5%±3% of total daily caloric intake;
4) polyunsaturated fat intake of about 3%±3% of total daily caloric intake;
5) complex carbohydrate intake of about 45%±5% of total daily caloric intake;

6) total caloric intake set at 15-20% less than said patient's daily energy expenditure; and 7) L-DOPA-containing foods (such as Broad beans) in an amount sufficient to ingest about 20-300 mg. of L-DOPA per day.

Nutrients that increase dopaminergic tone include L-DOPA, neuronal dopamine synthesis stimulators, neuronal postsynaptic dopaminergic receptor stimulators, neuronal presynaptic dopamine reuptake inhibitors, neuronal presynaptic dopamine receptor blockers, neuronal presynaptic dopamine release enhancers, dopamine degradation enzyme inhibitors, neuronal postsynaptic dopamine signal transduction stimulators, and combinations thereof.

Most preferably, the L-DOPA-containing foods in item (7) above are provided in an amount sufficient to ingest about 20-150 mg of L-DOPA per day. In one preferred embodiment, the L-DPOA-containing foods may be consumed throughout the day to effectuate a day-long rise in the circulating L-DOPA level.

As indicated above, Stage 2 includes the introduction of foods rich in L-DOPA (dihydroxyphenylalanine) such as broad beans, fava beans and the like. It is believed that such foods ingested following stage 1 of this nutritional regimen allow for a further increase in the central dopamine to norepinephrine activity ratio, and further improves metabolism by reducing parasympathetic and sympathetic activities towards normal. Ingestion of L-DOPA containing foods without the prior exposure to the Stage 1 diet of this plan will not provide benefit of improving the metabolic syndrome inasmuch as the L-DOPA will be converted to norepinephrine centrally, which could function to maintain the syndrome. A second advantage of this methodology for treating the metabolic syndrome is that metabolic rate decreases typically observed with other calorie restricting diets are not observed with this nutritional weight loss plan, thus allowing a gradual, steady and prolonged weight loss. Energy intake dispensation is channeled away from lipid synthesis (and storage) and towards protein turnover. Consequently, the body lean to fat mass ratio increases which helps deter the metabolic syndrome.

Stage 2 of the program may be modified to improve metabolism based again on surrogate marker test results. In general, periodic increases in monounsaturated fat and/or protein content of the diet may be necessary for the progression towards re-establishment of the normal neuroendocrine profile that maintains normal metabolism.

Like Stage 1, the length of time spent in Stage 2 is determined from the blood test results established prior to beginning the dietary regimen. In general, Stage 2 continues for approximately 4 to 6 months.

Preferably, at each stage during the program, simple sugars and/or high glycemic index carbohydrates are not to be consumed concurrently with saturated fats at a weight ratio greater than 1 carbohydrate to 4 saturated fat. In addition, in both Stage 1 or Stage 2, polyunsaturated fat intake may further comprise a ratio of omega-3 to omega-6 polyunsaturated fatty acids from between about 0.25:1 to about 2:1. In addition, it is preferred, but not required, that the food product be administered within 4 hours of waking in the morning.

In an alternative embodiment, a serotonin precursor may also be administered as part of the dietary regimen. Useful serotonin precursors include L-tryptophan, L-5-hydroxytryptophan, and the like. Useful doseages generally range from about 50 to about 2000 mg. Preferably, the serotonin precursor is administered in the evening before bedtime.

In order to assist the patient in consuming the proper foods at each stage of the dietary regimen, and to provide confidence that the patient is following the prescribed dietary regimen, the present invention also includes prepackaged meals and/or recipes that provide the proper balance of protein, carbohydrate, fat, total calories, and, if appropriate, the proper amount of L-DOPA. In one embodiment, the invention contemplates an article of manufacture comprising packaging material and one or more food products contained within the packaging material, wherein the one or more food products are effective for decreasing overactive CNS noradrenergic tone (Stage 1 of the above dietary regimen). The packaging material comprises a label which indicates that the food products can be used for treating the metabolic syndrome and/or related disorders in a patient, and wherein the food products comprise one or more of the following:

1) protein of about 25%±5% of total daily caloric intake of the patient;

2) monounsaturated fat of about 25%±5% of total daily caloric intake of the patient;

3) saturated fat of about 5%±5% of total daily caloric intake of the patient;

4) polyunsaturated fat of about 3%±5% of total daily caloric intake of the patient; and 5) complex carbohydrate of about 42%±7% of total daily caloric intake of the patient.

In another embodiment, the invention contemplates an article of manufacture comprising packaging material and one or more food products contained within the packaging material, wherein the food products are effective for increasing central dopamine to norepinephrine activity ratio (Stage 2 of the above dietary regimen). The packaging material comprises a label which indicates that the food products can be used for treating the metabolic syndrome and/or related disorders in a patient, and wherein the food products comprise one or more of the following:

1) protein of about 24%±5% of total daily caloric intake of the patient;

2) monounsaturated fat of about 23%±5% of total daily caloric intake of the patient;

3) saturated fat of about 5%±5% of total daily caloric intake of the patient;

4) polyunsaturated fat of about 3%±5% of total daily caloric intake of the patient;

5) complex carbohydrate of about 45%±5% of total daily caloric intake of the patient;

6) L-DOPA-containing food in an amount sufficient to ingest about 20-400, and more preferably about 20-300 mg. of L-DOPA per day.

In either embodiment of the articles of manufacture recited above, the polyunsaturated fat may further comprise a ratio of omega-3 to omega-6 polyunsaturated fatty acids from between about 0.25:1 to about 2:1.

As an alternative embodiment, the packaged food products may contain only part (e.g., one, two, or three) of the above-recited components with instructions for the patient to consume or obtain the remaining components from other sources (e.g., regular food). However, the total caloric value of the food products, in combination with regular food (if any), is approximately 0-25% less, and more preferably, 0-20% less, than the patient's daily energy expenditure.

In the above packaged food product embodiments, the present invention also contemplates including instructions on the label informing the purchaser how to consume the packaged food products in order to derive benefit from the dietary regimen. As defined herein, a food product include packaged foods, prepared meals, food bars, drinks, condiments, and the like.

The present invention is further described in detail by means of the following Example. All parts and percentages are by weight, and all temperatures are degrees Celsius unless explicitly stated otherwise.

EXAMPLE

Patients suffering from obesity or a related disorder such as hyperinsulinemia, insulin resistance, diabetes, hypertension, dyslipidemia, or metabolic syndrome are subjected to the following treatment program:
1. Obtain medical history of patient;
2. Conduct physical exam;
3. Calculate daily energy expenditure;
4. Determine ideal body weight;
5. Conduct blood work to determine the neuroendocrine status of the patient;
6. Devise Stage 1 nutritional plan and describe to patient;
7. Provide pre-packaged meals and/or recipes to patient to achieve Stage 1 nutritional goals;
8. Conduct weekly follow-up of patient compliance and general health;
9. Conduct blood work to determine response to Stage 1 nutritional plan, readiness for initiation of Stage 2 plan, and improvements in metabolic syndrome (e.g., changes in plasma glucose, insulin, total cholesterol, LDL cholesterol, and free fatty acid levels, body weight and blood pressure);
10. Provide pre-packaged meals and/or recipes to patient to achieve Stage 2 nutritional goals;
11. Conduct bi-weekly follow-up of subject compliance and general health;
12. Conduct blood work to evaluate the improvement to the neuroendocrine axis and metabolism; and
13. Conduct physical exam to evaluate improvement to general health and test for improvement in metabolic syndrome parameters.

Patients following the above regimen should observe gradual improvement in metabolism and a reduction in the symptoms of the metabolic syndrome, obesity, and Type 2 diabetes.

While the invention has been described in combination with embodiments thereof, it is evident that many alternatives, modifications and variations will be apparent to those skilled in the art in light of the foregoing description. Accordingly, it is intended to embrace all such alternatives, modifications and variations as fall within the spirit and broad scope of the appended claims. All patent applications, patents, and other publications cited herein are incorporated by reference in their entireties.

What is claimed is:

1. A method of treating a patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state, comprising the steps of:
   (a) providing to said patient suffering from a condition selected from the group consisting of metabolic syndrome, obesity, type 2 diabetes, pre-diabetes, hypertension, dyslipidemia, insulin resistance, endothelial dysfunction, pro-inflammatory state, and pro-coagulative state a food product that decreases overactive CNS noradrenergic tone;
   wherein said food product that decreases overactive CNS noradrenergic tone comprises:
   1) protein intake of about 25%±5% of total daily caloric intake;
   2) monounsaturated fat intake of about 25%±5% of total daily caloric intake;
   3) saturated fat intake of about 5%±5% of total daily caloric intake;
   4) polyunsaturated fat intake of about 3%±5% of total daily caloric intake;
   5) complex carbohydrate intake of about 42%±7% of total daily caloric intake; and
   6) total caloric intake set at 15-25% less than the said patient's daily energy expenditure; followed by
   (b) providing to said patient a food product that increases dopaminergic tone while maintaining said decreased overactive CNS noradrenergic tone;
   wherein said food product that increases dopaminergic tone while maintaining said decreased overactive CNS noradrenergic tone comprises:
   1) protein intake of about 24%±5% of total daily caloric intake;
   2) monounsaturated fat intake of about 23%±5% of total daily caloric intake;
   3) saturated fat intake of about 5%±5% of total daily caloric intake;
   4) polyunsaturated fat intake of about 3%±5% of total daily caloric intake;
   5) complex carbohydrate intake of about 45%±7% of total daily caloric intake;
   6) total caloric intake set at 0-25% less than said patient's daily energy expenditure; and
   7) L-DOPA-containing foods in an amount sufficient to ingest about 20-400 mg of L-DOPA per day; and
   wherein said polyunsaturated fat intake in each of steps (a) and (b) individually comprise a ratio of omega-3 to omega-6 polyunsaturated fatty acids from between about 0.25:1 to about 2:1; and
   wherein said providing step (a) continues for approximately 4 to 12 weeks; and wherein said providing step (b) continues for approximately 4 to 6 months.

2. The method of claim 1, wherein said L-DOPA-containing foods are present in an amount sufficient to ingest about 20-150 mg of L-DOPA per day.

3. The method of claim 1, wherein said L-DOPA-containing foods are ingested throughout the day to effectuate a day-long rise in circulating L-DOPA levels.

4. The method of claim 1, wherein in each of said food products in steps (a) and (b), simple sugars and/or high glycemic index carbohydrates are not provided concurrently with fats at a weight ratio greater than 1 carbohydrate to 4 saturated fat.

5. The method of claim 1, further comprising the step of establishing a baseline of metabolic activity in said patient by measuring the amounts of neuroendocrine compounds in said patient's blood prior to said providing steps.

6. The method of claim 5, wherein said neuroendocrine compounds are selected from the group consisting of plasma norepinephrine, insulin, dopamine, cortisol, morning urination, melatonin, plasma serotonin, and combinations thereof.

7. The method of claim 5, wherein said providing step (b) is implemented when plasma norepinephrine, and/or insulin levels are reduced by at least 20% relative to the levels established in said establishing step.

8. The method of claim 1, wherein step (b) is performed when said overactive CNS noradrenergic tone is decreased by at least 20%.

9. The method of claim 1, further comprising the step of administering between 50 and 2000 mg of a serotonin precursor to said patient before bedtime.

10. The method of claim 9, wherein said serotonin precursor is selected from the group consisting of L-tryptophan, L-5-hydroxytryptophan, and combinations thereof.

11. The method of claim 1, wherein said food product is administered within 4 hours of waking in the morning.

* * * * *